United States Patent [19]

Valle

[11] Patent Number: 4,493,827

[45] Date of Patent: Jan. 15, 1985

[54] METHOD OF INDUCING SLEEP

[76] Inventor: Ronald Valle, 44 Fitch St., Carteret, N.J. 07008

[21] Appl. No.: 551,144

[22] Filed: Nov. 14, 1983

[51] Int. Cl.³ ................ A61K 31/135; A61K 31/161; A61K 33/02

[52] U.S. Cl. .................................... 424/166; 424/324; 424/330

[58] Field of Search ........................ 424/166, 324, 330

[56] References Cited

U.S. PATENT DOCUMENTS 4,260,600  4/1981  Valle .................................. 424/166

Primary Examiner—Stanley J. Friedman

[57] ABSTRACT

Inducing sleep using acetaminophen, phenylephrine, phenylpropanolamine phenyltoloxamine dihydrogen citrate and ammonium chloride.

3 Claims, No Drawings

METHOD OF INDUCING SLEEP

BACKGROUND OF INVENTION

This invention relates to a method of inducing sleep in a human being (patient) who is physically and mentally exhausted by administering to said patient several active compounds forming a pharmaceutical combination. The compounds which form this pharmaceutical combination are all known and are known for their adrenergic, antihistamine, analgesic or antipyretic uses, such as, for example, to relieve symptoms of a common cold.

I have found that by using a particular combination of these compounds, in a particular dosage range, a sleep-inducing effect results. As such, using my combination for this use avoids the use of other well-known, costly, prescription-only sleep inducers with their resultant potentially dangerous and, in many cases, unknown side effects and habit forming tendencies. The compounds which make up my combination are readily available, are quite safe for their uses, and are not as costly as the prescription sleep inducers.

It is generally known that one who is exhausted, that is, one who is in a mentally and/or physically exhausted state, may and usually does find difficulty in sleeping. The use of the combination of drugs described herein for inducing sleep behaves as if the adrenaline in a patient is reduced leading to a natural sleepy state.

This use differs from the use described in my U.S. Pat. No. 4,260,600 granted Apr. 7, 1981, in that a tranquilizing use is taught in said patent and normal sleep associated with tranquilizing effects comes about when a patient who has had sufficient sleep is caused to fall asleep again. The present use of inducing sleep relates only to a person who is physically and/or mentally exhausted to begin with and has difficulty in falling asleep.

The compounds to be administered are as follows:

(1) Phenylephrine hydrochloride which is (R)-3-hydroxy-α-[(methylamino)methyl]benzenemethanol hydrochloride. This compound alone has a therapeutic use as an adrenergic.

(2) Phenylpropanolamine hydrochloride which is chemically known as α-(1-aminoethyl)benzenemethanol hydrochloride. This compound when administered alone or in its hydrochloride salt form is an adrenergic (vasoconstrictor) agent also.

(3) Phenyltoloxamine which is N,N-dimethyl-2-[2-phenylmethyl)phenoxy]ethanamine. This compound when administered as the dihydrogen citrate salt is useful as an antihistamine.

(4) Acetaminophen which is N-(4-hydroxyphenyl)-acetamide. This compound when administered alone is useful as an analgesic or antipyretic.

(5) Ammonium Chloride. This compound when administered alone has a therapeutic use in the pharmaceutical field as a systemic acidifier.

All the above compounds and their listed therapeutic uses in the pharmaceutical field are known from the prior art, i.e., all are disclosed in The Merck Index, Ninth Edition.

I have found, however, that these compounds or combinations thereof when administered to a patient who is physically and mentally exhausted in dosage ranges listed below have a sleep inducing effect. This combination of drugs (compounds as described more fully below) when administered in the proportions listed below induce sleep in a patient who is in a physically and mentally exhausted state.

The combination of compounds of this invention can be administered in capsule form or they may be compressed into tablets using conventional pharmaceutical excipients, binders and lubricants and with or without other adjuncts. In fact, several of the active ingredients listed above come in commercially available cold and cough tablets and several examples of typical tablets are described. The compounds are preferably administered orally in daily amounts as follows:

Acetaminophen—100-1000 mg/day,
Phenylephrine hydrochloride—1-10 mg/day,
Phenylpropanolamine—5-30 mg/day,
Phenyltoloxamine dihydrogen citrate—5-30 mg/day,
Ammonium Chloride—50-1000 mg/day.

A daily specific dose of the following compounds administered to a physically and mentally exhausted patient in need of sleep is exemplified below:

Acetaminophen—520 mg/day,
Phenylephrine hydrochloride—5 mg/day,
Phenylpropanolamine—20 mg/day,
Phenyltoloxamine dihydrogen citrate—25 mg/day,
Ammonium Chloride—320-480 mg/day.

A typical commercially available cough tablet contains the following ingredients:

Acetaminophen—260 mg.
Phenylephrine HCl—2.5 mg.
Phenylpropanolamine hydrochloride—10 mg.
Phenyltoloxamine—12.5 mg.
Vitamin C—20 mg.

and a glyceryl guaiacolate base.

Typical contents of another commercially available cough tablet:

Ammonium chloride—80 mg.

and a citric acid in a sugar base.

In order to obtain the specific dosage listed above, a patient needing sleep because of physical and mental exhaustion can take two tablets during a 24-hour period of the first listed commercially available cough tablet and 4-6 tablets every 24 hours of the second commercially available cough tablet.

The compounds described in this invention are advantageously administered at a dosage range as described or a somewhat higher or lower dosage as the conditions warrant. It will be realized by those skilled in the art that the dosage range for any particular patient or human will depend on the severity of the mental or physical exhaustion and the need for inducing sleep, the weight of the patient and any other condition which a physician or other person skilled in the art will take account of.

What is claimed is:

1. A method of inducing sleep in a patient who is mentally or physically exhausted which comprises administering to a patient in need of such sleep inducing a pharmaceutically effective combination of the following compounds in the following daily dosages:

Acetaminophen—100-1,000 mg/day,
Phenylephrine hydrochloride—1-10 mg/day,
Phenylpropanolamine—5-30 mg/day,
Phenyltoloxamine dihydrogen citrate—5-30 mg/day,
Ammonium chloride—50-1,000 mg/day.

2. A method of inducing sleep in a patient who is mentally or physically exhausted which comprises administering to a patient in need of such sleep inducing a pharmaceutically effective combination of the following compounds in the following daily dosage:
Phenylephrine hydrochloride—1-10 mg/day,
Phenylpropanolamine—5-30 mg/day,
Phenyltoloxamine dihydrogen citrate—5-30 mg/day,
Ammonium chloride—50-1,000 mg/day.

3. A method of inducing sleep in a patient who is mentally or physically exhausted which comprises administering to a patient in need of such sleep inducing a pharmaceutically effective combination of the following compounds in the following daily dosages:
Phenylephrine hydrochloride—1-10 mg/day,
Phenylpropanolamine—5-30 mg/day,
Ammonium chloride—50-1,000 mg/day.

* * * * *